United States Patent
Modi

(10) Patent No.: US 9,833,461 B2
(45) Date of Patent: Dec. 5, 2017

(54) THERAPEUTIC COMPOSITIONS COMPRISING CANNABIDIOL AND CORTICOSTEROIDS

(71) Applicant: Pankaj Modi, Ancaster (CA)

(72) Inventor: Pankaj Modi, Ancaster (CA)

(73) Assignee: CTT Pharma Inc., Stoney Creek (CA)

( * ) Notice: Subject to any disclaimer, the term of this patent is extended or adjusted under 35 U.S.C. 154(b) by 0 days.

(21) Appl. No.: 14/921,501

(22) Filed: Oct. 23, 2015

(65) Prior Publication Data

US 2017/0112855 A1 Apr. 27, 2017

(51) Int. Cl.
*A61K 31/573* (2006.01)
*A61K 31/05* (2006.01)
*A61K 31/352* (2006.01)
*A61K 9/00* (2006.01)

(52) U.S. Cl.
CPC .......... *A61K 31/573* (2013.01); *A61K 9/0014* (2013.01); *A61K 9/0053* (2013.01); *A61K 31/05* (2013.01); *A61K 31/352* (2013.01)

(58) Field of Classification Search
CPC .... A61K 31/05; A61K 31/352; A61K 31/573; A61K 9/0014; A61K 9/0053
See application file for complete search history.

(56) References Cited

U.S. PATENT DOCUMENTS

| | | | | |
|---|---|---|---|---|
| 8,623,401 | B2 * | 1/2014 | Modi | A61K 9/0056 424/441 |
| 2009/0004275 | A1 * | 1/2009 | Martyn | A61K 9/006 514/1.1 |
| 2011/0195096 | A1 * | 8/2011 | Kindler | A61K 31/20 424/400 |

* cited by examiner

*Primary Examiner* — Savitha Rao
(74) *Attorney, Agent, or Firm* — Gowling WLG (Canada) LLP

(57) ABSTRACT

A composition comprising a tetrahydrocannabinoid compound, a second cannabinoid and a corticosteroid is provided. The composition is useful to treat psoriasis and related conditions in a mammal.

14 Claims, 1 Drawing Sheet

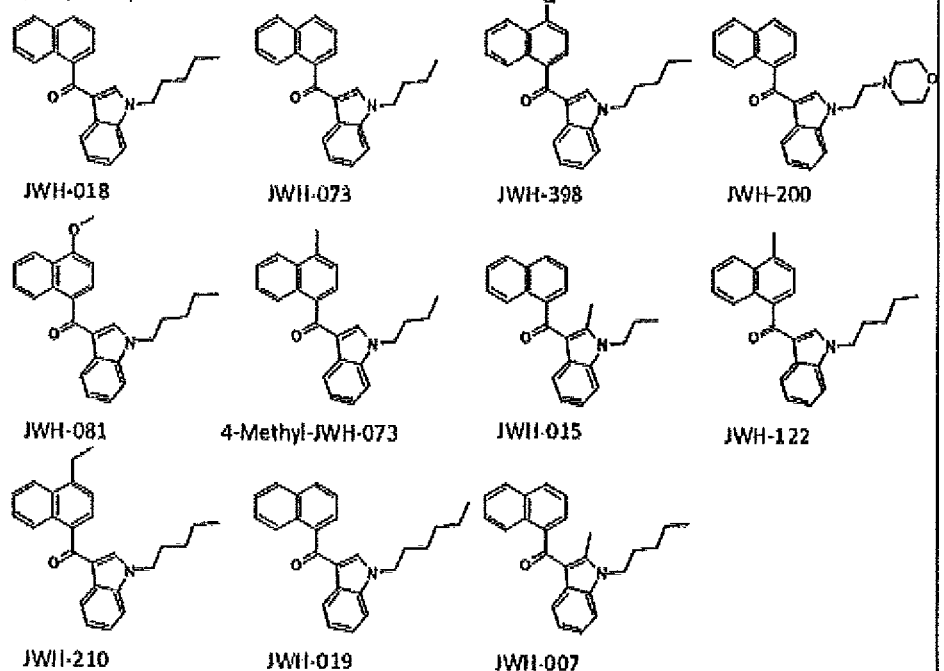

THERAPEUTIC COMPOSITIONS COMPRISING CANNABIDIOL AND CORTICOSTEROIDS

FIELD OF THE INVENTION

The present invention generally relates to therapeutic composition comprising one or more cannabinoids, and use of the composition to treat certain ailments, including psoriasis.

BACKGROUND OF THE INVENTION

Psoriasis is a chronic immune-mediated disease that generally appears on the skin. It occurs when the immune system sends out faulty signals that speed up the growth cycle of skin cells. There are five types of psoriasis: plaque, guttate, inverse, pustular and erythrodermic. The most common form, plaque psoriasis, is commonly seen as red and white hues of scaly patches appearing on the top first layer of the epidermis (skin). Psoriasis is a chronic recurring condition that varies in severity from minor localized patches to complete body coverage. Fingernails and toenails are frequently affected (psoriatic nail dystrophy). Psoriasis can also cause inflammation of the joints, which is known as psoriatic arthritis. Between ten and forty percent of all people with psoriasis have psoriatic arthritis. The cause of psoriasis is not fully understood, but it is believed to have a genetic component. Various environmental factors may aggravate psoriasis, including stress, and withdrawal of systemic corticosteroid.

There are many treatments available, but because of its chronic recurrent nature, psoriasis is a challenge to treat. Accordingly, it would be desirable to develop a novel composition useful to treat psoriasis and related conditions.

SUMMARY OF THE INVENTION

It has now been found that a combination of a tetrahydrocannabinoid compound, a second cannabinoid and a steroid are useful to treat psoriasis and related conditions.

Thus, in one aspect of the invention a composition comprising a tetrahydrocannabinoid compound, a second cannabinoid and a corticosteroid is provided.

In another aspect, a method of treating psoriasis and related conditions in a mammal is provided comprising administering to the mammal a composition comprising a tetrahydrocannabinoid compound, a second cannabinoid and a corticosteroid.

These and other aspects of the invention are described by reference to the following FIGURE.

BRIEF DESCRIPTION OF THE FIGURE

FIG. 1 illustrates chemical structures of cannabinoid compounds.

DETAILED DESCRIPTION OF THE INVENTION

A formulation comprising a tetrahydrocannabinoid compound, at least one second cannabinoid and a corticosteroid is provided.

The term "tetrahydrocannabinoid compound" refers to a group of related compounds and analogs thereof, namely, delta-9 tetrahydrocannabinol (THC) and functionally equivalent compounds, including analogs and derivatives thereof such as delta-8 tetrahydrocannabinol (D8-THC), tetrahydrocannabinol acid (THCA), tetrahydrocannabivarin (THCV), tetrahydrocannabivarin acid (THCVA), nabilone, rimonabant (SR141716), JWH-018, JWH-073, CP-55940, dimethylheptylpyran, HU-210, HU-331, SR144528, WIN 55,212-2, JWH-133, levonantradol and AM-2201. The term "functionally equivalent" as it relates to analogs and derivatives of THC refers to compounds which exhibit the same or similar therapeutic effect of THC.

The term "a second cannabinoid" refers to a cannibinoid other than a tetrahydrocannabinoid. Examples of a second cannibinoid include, but are not limited to, cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), naphthoylindoles such as JWH-018, JWH-073, JWH-398, JWH-200, JWH-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenoles such as CP 47,497-C8 and CP 47,497; and HU-210. FIG. 1 illustrates chemical structures of a number of these compounds.

Cannabinoids may be extracted from the *cannabis* plant using methods well-established in the art. Many of the cannibinoids may also be prepared using standard chemical synthetic methods. Some of these compounds are also commercially available.

The term "corticosteroid" refers to steroid hormones that are produced in the adrenal cortex of vertebrates as well as the synthetic analogues of these hormones. Examples include, but are not limited to, clobetasol, betamethasone, haltobetasol, fluocinonide, flurandrrenolide, mometasone, diflorasone, halcinonide, desoximetasone and fluticasone. Corticosteroids are commercially available in various forms. Non-limiting examples include: Clobex Lotion/Spray/Shampoo (0.05% Clobetasol propionate), Cormax Cream/Solution (0.05% Clobetasol propionate), Diprolene Ointment, 0.05% Augmented betamethasone, Olux E Foam, 0.05% Clobetasol propionate, Olux Foam, 0.05% Clobetasol propionate, Temovate Cream/Ointment/Solution, 0.05% Clobetasol propionate, Ultravate Cream/Ointment, 0.05% Halobetasol propionate, Vanos Cream, 0.1% Fluocinonide, Cordran Tape, 0.05% Flurandrenolide, Diprolene Cream AF, 0.05% Augmented betamethasone, Elocon Ointment, 0.1% Mometasone furoate, Florone Ointment, 0.05% Diflorasone diacetate, Halog Ointment/Cream, 0.1% Halcinonide, Lidex Cream/Gel/Ointment, 0.05% Fluocinonide, Psorcon E Cream, 0.05% Diflorasone diacetate, Topicort Cream/Ointment, 0.25% Desoximetasone, Topicort Gel, 0.05% Desoximetasone, Cutivate Ointment, 0.005% Fluticasone propionate, Lidex-E Cream, 0.05% Fluocinonide, Luxiq Foam, 0.12% Betamethasone valerate and Topicort LP Cream, 0.05% Desoximetasone.

The present composition will generally comprise the tetrahydrocannabinoid in an amount in the range of about 1-10% by wt, the second cannabinoid in an amount in the range of about 1-10% by wt and the corticosteroid in an amount in the range of about 0.01-10% by wt. Thus, in one embodiment, the composition comprises tetrahydrocannabinoid in an amount in the range of about 1-10% by wt, e.g. between about 4-6% by wt, the a second cannabinoid in an amount in the range of about 1-10% by wt, e.g. between about 4-6% by wt, and the corticosteroid in an amount in the range of about 0.01-1% by wt. In a preferred embodiment, the composition comprises the tetrahydrocannabinoid in an amount of about 5% by wt, the a second cannabinoid in an amount of about 5% by wt and the corticosteroid in an amount of about 0.05% by wt. The term "about" is used herein to mean an amount that may differ somewhat from the given value, by an amount that would not be expected to significantly affect activity or outcome as appreciated by one of skill in the art, for example, a variance of from 1-10% from the given value.

The present composition may be combined with one or more pharmaceutically acceptable adjuvants or carriers. The expression "pharmaceutically acceptable" means acceptable for use in the pharmaceutical arts, i.e. not being unacceptably toxic, or otherwise unsuitable for administration to a mammal. Examples of pharmaceutically acceptable adjuvants include, but are not limited to, diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for oral administration via tablet, capsule, lozenge, solution or suspension in an aqueous or non-aqueous liquid, an oil-in-water or water-in-oil liquid emulsion, an elixir or syrup are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered traganeanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, disintegrating agents, anti-oxidants, preservatives, colouring agents and flavouring agents may also be present.

A particularly useful oral formulation is an orally administrable wafer, which generally exhibits a very high rate of dissolution and, thus, provides rapid absorption of the present composition. The wafer may comprise at least one physiologically acceptable film forming agent such as pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, polyacrylic acid, glycolide, polylactide, methylmethacrylate copolymer, carboxyvinyl polymer, amylose, high amylose starch, hydroxypropylated high amylose starch, dextrin, pectin, chitin, ehitosan, levan, elsinan and mixtures thereof. Secondary film forming agents may be added to the formulation to optimize wafer characteristics such as tensile strength, stability, flexibility and brittleness including agents such xanthan gum, tragacanth gum, guar gum, locust bean gum, acacia gum, arabic gum, collagen, gelatin, zein, gluten, soy protein isolate, whey protein isolate, casein and mixtures thereof. The wafer may also include one or more adjuvants selected from the group consisting of: a plasticizing agent, a flavoring agent, a sulfur precipitating agent, a saliva stimulating agent, a cooling agent, a surfactant, a stabilizing agent, an emulsifying agent, a thickening agent, a binding agent, a coloring agent, a sweetener, and a fragrance.

Preferably, the orally administrable wafer comprises at least about 30 to about 80 wt % film forming agent, such as pullulan, or a mixture of pullulan with one or more other film forming agents such as polyvinyl alcohol, carrageenan, guar gum, xanthan gum and locust bean gum. In one embodiment, the wafer comprises PEG in an amount of less than about 5 wt %.

Various methods for making such wafers may be applied, including the method described in U.S. Pat. No. 8,623,401, the contents of which are incorporated herein by reference. Generally, to make a wafer, the selected film-forming agents are dissolved in an aqueous solution with the present cannabinoid-containing composition, including any desired adjuvants, to form a gel. The gel is then formed into a thin layer and exposed to a plurality of heating and/or cooling cycles, for example, for a period of no more than about 3 minutes, to result in a product that can be formed into suitable wafers. The wafer generally exhibits a very high rate of dissolution, e.g. a dissolution rate of at least about 2 milligrams/sec, in an aqueous environment. Due to its high rate of dissolution, the wafer accordingly exhibits a very desirable rate of delivery of drug, i.e. $T_{max}$ the amount of time following administration of the wafer for the drug it contains to reach its maximum plasma concentration. For example, $T_{max}$ for delivery of the present cannabinoid composition may be more than about 10 minutes, and preferably less than 10 minutes, e.g. 8 minutes or less.

In another embodiment, an orally administrable may be prepared by dissolving the selected film-forming agent(s) in an aqueous solution in combination with the present cannabinoid-containing composition and any desired adjuvants, with stirring and heat, to form a gel. The gel is then spread as a thin layer, e.g. about 10 microns or less, and allowed to cool. Wafers may then be formed therefrom.

In another embodiment, the composition may be formulated for application topically as a cream, lotion or ointment. For such topical application, the composition may include an appropriate base such as a triglyceride base. Such creams, lotions and ointments may also contain a surface active agent and other cosmetic additives such as skin softeners (e.g. aloe vera) and the like as well as fragrance. As will be appreciated by one of skill in the art, a topical formulation may also be administered via a transdermal patch, bandage or cloth. Aerosol formulations, for example, for nasal delivery, may also be prepared in which suitable propellant adjuvants are used. Compositions of the present invention may also be administered as a bolus, electuary, or paste. Compositions for mucosal administration are also encompassed, including oral, nasal, rectal or vaginal administration for the treatment of infections which affect these areas. Such compositions generally include one or more suitable non-irritating excipients or carriers comprising, for example, cocoa butter, polyethylene glycol, a suppository wax, a salicylate or other suitable carriers. Other adjuvants, such as preservatives, anti-microbial agents and the like, may also be added to the composition regardless of how it is to be administered which, for example, may aid to extend the shelf-life thereof.

In one embodiment, a topical formulation is prepared by combining the present cannabinoid-containing composition with one or more transcutaneous carriers selected from the group consisting of water, short carbon chain alcohols such as tert-butyl alcohol, tert-butyl alcohol, 1,3-butanediol, tert-amyl alcohol, 3-methyl-3-pentanol, ethchlorvynol, 1-octanol (capryl alcohol), pelargonic alcohol (1-nonanol), 1-decanol (decyl alcohol, capric alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1- ol), heptadecyl alcohol (1-n-heptadecanol, heptadecanol), stearyl alcohol (1-octadecanol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), 1-heptacosanol, montanyl alcohol, cluytyl alcohol, or 1-octacosanol, 1-nonacosanol and myricyl alcohol, melissyl alcohol, or 1-triacontanol, or glycerol; dimethysulfoxide, and its derivatives; film forming agents as described above, surfactant such as an alkali metal edidate, e.g. sodium lauryl sulfate, polyoxyethylene lauryl ether and derivatives; emulsifiers such as sodium lauryl sulfate, polyoxyethylene (40) stearate, stearic acid and lecithin; anti-inflammatory agents such as niacinamide; skin conditioning/softening agents and emollients such as aloe vera, linoleic acid, vitamin E and the acetate thereof, and crodamol sts; absorption enhancers such as polyoxyethylene compounds and/or derivatives; antimicrobial agents; preservatives and stabilizers (such as phenoxyethanol) and excipients such as polyethylene glycol, polypropylene glycol, glycerin, oils such as mineral oil, olive oil, sesame oil, castor oil and the like, and mixtures thereof. As one of skill in the art will appreciate, the topical formulation may include additional adjuvants and excipients which enhance the utility of the formulation for topical use.

The components of the topical formulation may be combined in phases to result in a formulation suitable to topical administration. For example, a first phase (phase A) including transcutaneous carriers such as water and/or an alcohol, an emulsifier (e.g. an alkali metal edidate such as sodium lauryl sulfate), and skin agents (e.g. aloe compounds) may be combined. A second phase (phase B) may include a carrier (e.g. alcohol), oils, absorption enhancer and/or emollient. Additional phases may include other suitable adjuvants including surfactants, emollients, absorption enhancers, oils, anti-inflammatory agents, skin agents, stabilizers and anti-microbial agents (e.g. germicides, biocides and the like such as diocide). Thus, a first additional phase may include one or more skin agents (e.g. linoleic acid, acetate compounds), oils and absorption enhancers; a second additional phase may include one or more emulsifiers, phospholipids and absorption enhancers; and another additional phase may include one or more anti-microbial agents and stabilizers.

The transcutaneous carrier or mixture of carriers is present in the topical formulation in an amount of up to about 50-60% by wt of the formulation. Other components are present in an amount in the range of about 1-10% by wt; however, as one of skill in the art will appreciate amounts of such other components outside of this range is acceptable as well, particularly if there is a combination of like components, e.g. two or more surfactants, two or more emollients, two or more skin agents, etc.

In other embodiments, the present composition may be formulated for administration by routes including, but not limited to, oral, intranasal, enteral, topical, sublingual, intra-arterial, intramedullary, intrauterine, intrathecal, inhalation, ocular, transdermal, vaginal or rectal routes, and will include appropriate carriers in each case.

The present composition is useful to treat psoriasis and related conditions, including but not limited to, joint pain, muscle pain, and arthritis resulting from or related to the psoriasis in a mammal. The term "mammal" is used herein to refer to human and non-human mammals. Generally, the composition is administered at least daily, and optionally 1-3 times daily, depending on the severity of the condition being treated. Topical formulations are applied to the target site, i.e. the affected epidermal site, or site of pain. Treatment is continued until the condition is resolved, e.g. the affected epidermis has essentially returned to normal, and any pain and/or irritation has either ceased or been reduced to an acceptable degree.

Embodiments of the invention are described in the following specific examples which are not to be construed as limiting.

Example 1—Treatment of Psoriasis with a Topical Formulation

A topical formula was prepared including the following ingredients:

| Cat.# | Ingredients | % by wt of the formula |
|---|---|---|
| PHASE A | | |
| 265 | Water | 29.680% |
| 629 | sodium lauryl sulfate | 0.750% |
| 366 | versene na2 | 0.050% |
| 171 | aloe vera 200 x powder | 5.000% |
| 86 | Glycerin | 4.550% |
| 35 | butylene glycol | 2.000% |
| PHASE B | | |
| 229 | stearic acid | 11.00% |
| 044 | glyceryl stearate se | 2.820% |
| 539 | castor oil | 0.480% |
| 483 | olive oil | 1.000% |
| 214 | Dimethicone | 0.400% |
| 151 | myrj 52 (polyoxyethylene (40) stearate) | 3.580% |
| 2030 | crodamol sts | 1.890% |
| 559 | sesame oil | 3.000% |
| PHASE C | | |
| 1420 | linoleic acid | 3.750% |
| 260 | tocopherol acetate | 2.500% |
| 296 | lactic acid 88% | 5.700% |
| 933 | Niacinamide | 5.500% |
| 331 | evening primrose oil | 2.000% |
| PHASE D | | |
| 125 | lecithin (sphingocide or (phospholipon g) | 2.000% |
| 2218 | brij 35 (polyoxyethylene lauryl ether) | 0.750% |
| PHASE E | | |
| 244 | Phenoxyethanol | 0.500% |
| 1207 | Diocide | 0.500% |
| PHASE F | | |
| 237 | Tea | 0.500% |
| PHASE G | | |
| | mometasone 0.05% + THC 5% + CBD 5% | 10.05% |
| | | 100.000% |

Mix ingredients of Phase A together with heating to 60° C. and continuous stirring. Mix ingredients of Phase B together with heating at 65° C. and continuous stirring at high speed. Add active drug component (Phase G) to Phase B slowly with continuous stirring until the mixture is homogenous. Add the homogenous mixture (Phase B and G) to Phase A, slowly stirring at high speed at 65° C. Slowly add each of Phase C, D E and F to this mixture at 65° C. with high speed stirring. Remove heat and cool mixture slowly to room temperature to make a cream. This cream was found to be stable at room temperature as no separation was observed over 90 days. The cream was placed in 5 mL double coated film tube and sealed for future use.

Subjects with severe to moderate psoriasis were screened for the treatment. Selected subjects were asked to stop all other treatments for 48 hours prior to the start of the trial. Treatment included application of the cream, in an amount of about 0.5 mL to 1 mL by volume, topically to an affected site twice a day, once in the morning and once at the bed time.

All subjects reported excellent relief from the painful symptoms, most within 24 hours of starting the treatment.

Example 2—Treatment of Psoriasis with an Oral Formulation

Oral fast dissolving wafers were made by combining the following ingredients with stirring and heat:

| Ingredient | Weight (grams) |
|---|---|
| Xanthan Gum | 1.076 |
| Locust Bean Gum | 0.215 |
| Carrageenan | 1.073 |
| Pullulan | 57.578 |
| Deionized Water | 31.258 |
| BHT (hydroxybutyl toluene) | 0.03 |
| Glycerine | 3 |
| Mineral Oil | 3 |
| Polysorbate 80 | 0.4 |
| Atlas 3000/Atmos300 | 0.4 |
| Mometasone 0.05% + THC 5% + CBD 5% | 2.0 |

Once combined to form a homogeneous mixture, the mixture was spread to form a thin layer (e.g. 10 microns or less) and then cooled in a forced air oven for 30 min at 87° C. to form a product that may be formed into an oral wafer.

Subjects with severe to moderate psoriasis were screened for the treatment. Selected subjects were asked to stop all other treatments for 48 hours prior to the start of the trial. Each subject took one wafer in the morning and one in the evening, each containing mometasone 0.05%+THC 5%+CBD 5%.

All subjects reported excellent relief from the painful symptoms, most within 24 hours of starting the treatment.

The invention claimed is:

1. A composition formulated for oral administration comprising:
   i) a tetrahydrocannabinoid compound or functionally equivalent synthetic derivative thereof selected from the group consisting of delta-9 tetrahydrocannabinol (THC), delta-8 tetrahydrocannabinol (D8-THC), tetrahydrocannabinol acid (THCA), tetrahydrocannabivarin (THCV), tetrahydrocannabivarin acid (THCVA), nabilone, rimonabant (SR141716), JWH-018, JWH-073, CP-55940, dimethylheptylpyran, HU-210, HU-331, SR144528, WIN 55,212-2, JWH-133, levonantradol and AM-2201;
   ii) a second cannabinoid or functionally equivalent synthetic derivative thereof selected from the group consisting of cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), JWH-018, JWH-073, JWH-398, JWH-200, JWH-081, 4-methyl-JWH-073, JWH-015, JWH-122, JWH-220, JWH-019, JWH-007, JWH-250, JWH-203, RCS-4, AM-694, WIN 48,098, CP 47,497-C8, CP 47,497 and HU-210; and
   iii) a corticosteroid,
   wherein the composition is a wafer that exhibits a $T_{max}$, of less than 10 minutes, said wafer being formed by combining the tetrahydrocannabinoid, second cannabinoid and corticosteroid with an aqueous solution comprising at least about 30 to 80 wt % of a film forming agent selected from pullulan, or a mixture of pullulan with one or more other film forming agents to form a gel that is spread and dried to form the wafer.

2. The composition of claim 1, comprising the tetrahydrocannabinoid in an amount in the range of about 1-10% by wt, the second cannabinoid in an amount in the range of about 1-10% by wt and the corticosteroid in an amount in the range of about 0.01-10% by wt.

3. The composition of claim 2, comprising the tetrahydrocannabinoid in an amount in the range of about 4-6% by wt, the second cannabinoid in an amount in the range of about 4-6% by wt and the corticosteroid in an amount in the range of about 0.01-1% by wt.

4. The composition of claim 1, wherein the corticosteroid is selected from the group consisting of clobetasol, betamethasone, haltobetasol, fluocinonide, flurandrrenolide, mometasone, diflorasone, halcinonide, desoximetasone and fluticasone.

5. The composition of claim 1, comprising THC, cannabidiol and mometasone.

6. The composition of claim 1, wherein the other film forming agent is selected from the group consisting of polyvinyl alcohol, carboxymethylcellulose, carrageenan, guar gum, gelatin, xanthan gum, agar and locust bean gum.

7. A method of treating psoriasis and related conditions in a mammal comprising administering to the mammal a composition as defined in claim 1.

8. The method of claim 7, wherein the composition comprises the tetrahydrocannabinoid in an amount in the range of about 1-10% by wt, the second cannabinoid in an amount in the range of about 1-10% by wt and the corticosteroid in an amount in the range of about 0.01-10% by wt.

9. The method of claim 7, wherein the corticosteroid is selected from the group consisting of clobetasol, betamethasone, haltobetasol, fluocinonide, flurandrrenolide, mometasone, diflorasone, halcinonide, desoximetasone and fluticasone.

10. The method of claim 7, wherein the composition is orally administered.

11. The method of claim 7, wherein the composition comprises THC, cannabidiol and mometasone.

12. The composition of claim 1, wherein said other film-forming agent is at least one of polyvinyl alcohol, carrageenan, guar gum, xanthan gum and locust bean gum.

13. The composition of claim 1, which comprises polyethylene glycol in an amount of less than about 5 wt %.

14. The composition of claim 1, wherein the wafer exhibits a dissolution rate of at least about 2 milligrams/second in an aqueous environment.

* * * * *